United States Patent
Smoter

(12) 
(10) Patent No.: US 10,897,941 B1
(45) Date of Patent: Jan. 26, 2021

(54) UNDERGARMENT WITH INTEGRAL SANITARY LINER

(71) Applicant: Rosemary Smoter, Milford, MI (US)

(72) Inventor: Rosemary Smoter, Milford, MI (US)

( * ) Notice: Subject to any disclaimer, the term of this patent is extended or adjusted under 35 U.S.C. 154(b) by 66 days.

(21) Appl. No.: 16/423,309

(22) Filed: May 28, 2019

(51) Int. Cl.
*A41D 31/12* (2019.01)
*A41B 9/00* (2006.01)

(52) U.S. Cl.
CPC .............. *A41D 31/12* (2019.02); *A41B 9/001* (2013.01); *A41B 2300/22* (2013.01); *A41B 2300/35* (2013.01); *A41B 2400/60* (2013.01)

(58) Field of Classification Search
CPC ................................ A41D 31/12; A41B 9/001
USPC ............................................................. 2/406
See application file for complete search history.

(56) References Cited

U.S. PATENT DOCUMENTS

| | | | |
|---|---|---|---|
| 3,613,686 A | 10/1971 | Woskin | |
| 4,236,257 A * | 12/1980 | Williams | A41B 9/04 2/406 |
| 4,244,059 A * | 1/1981 | Pflaumer | A41B 9/004 2/400 |
| 4,555,245 A * | 11/1985 | Armbruster | A61F 5/4401 2/403 |
| 4,813,950 A * | 3/1989 | Branch | A61F 13/49006 2/401 |
| 5,098,419 A * | 3/1992 | Gold | A41B 9/004 2/401 |
| 5,846,607 A * | 12/1998 | Hurley | B05D 1/18 427/374.2 |
| 6,041,446 A * | 3/2000 | Braunstein | A41B 9/004 2/400 |
| D649,330 S | 11/2011 | Trahin | |
| 8,123,735 B2 * | 2/2012 | Deerin | A61F 13/74 604/396 |
| 8,460,265 B1 * | 6/2013 | Calender | A61F 13/49006 604/396 |
| 2008/0125737 A1 | 5/2008 | Modgeddi | |
| 2011/0197345 A1 * | 8/2011 | Hutchins Adams | A41B 9/04 2/406 |

FOREIGN PATENT DOCUMENTS

EP 2412353 2/2012

* cited by examiner

*Primary Examiner* — Gloria M Hale

(57) ABSTRACT

The undergarment with an integral sanitary liner is an article of loin wear. A patient wears the undergarment with an integral sanitary liner when the patient anticipates liquid discharge in the loin region. The undergarment with an integral sanitary liner is an absorbent structure that absorbs liquid discharges in the loin region. The undergarment with an integral sanitary liner comprises an anterior panel, a posterior panel, an inferior panel, an elastic webbing, a liner, and a plurality of seams. The plurality of seams interconnect the anterior panel, the posterior panel, the inferior panel, and the elastic webbing to form the article of loin wear. The inferior panel forms the absorbent structure of the undergarment with an integral sanitary liner of the article of loin wear. The liner is a sheeting that protects the patient from the liquids in the inferior panel.

16 Claims, 6 Drawing Sheets

UNDERGARMENT WITH INTEGRAL SANITARY LINER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including bandages and dressings, more specifically, an absorbent pad integrally incorporated into an undergarment. (A61F13/15)

SUMMARY OF INVENTION

The undergarment with an integral sanitary liner is an article of loin wear. The undergarment with an integral sanitary liner is adapted for use by a patient. The patient wears the undergarment with an integral sanitary liner when the patient anticipates liquid discharge in the loin region. The undergarment with an integral sanitary liner is an absorbent structure that absorbs liquid discharges in the loin region. The undergarment with an integral sanitary liner comprises an anterior panel, a posterior panel, an inferior panel, an elastic webbing, a liner, and a plurality of seams. The plurality of seams interconnect the anterior panel, the posterior panel, the inferior panel, and the elastic webbing to form the article of loin wear. The inferior panel forms the absorbent structure of the undergarment with an integral sanitary liner of the article of loin wear. The liner is a sheeting that protects the patient from the liquids in the inferior panel. The article of loin wear is machine washable.

These together with additional objects, features and advantages of the undergarment with an integral sanitary liner will be readily apparent to those of ordinary skill in the art upon reading the following detailed description of the presently preferred, but nonetheless illustrative, embodiments when taken in conjunction with the accompanying drawings.

In this respect, before explaining the current embodiments of the undergarment with an integral sanitary liner in detail, it is to be understood that the undergarment with an integral sanitary liner is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the undergarment with an integral sanitary liner.

It is therefore important that the claims be regarded as including such equivalent construction insofar as they do not depart from the spirit and scope of the undergarment with an integral sanitary liner. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
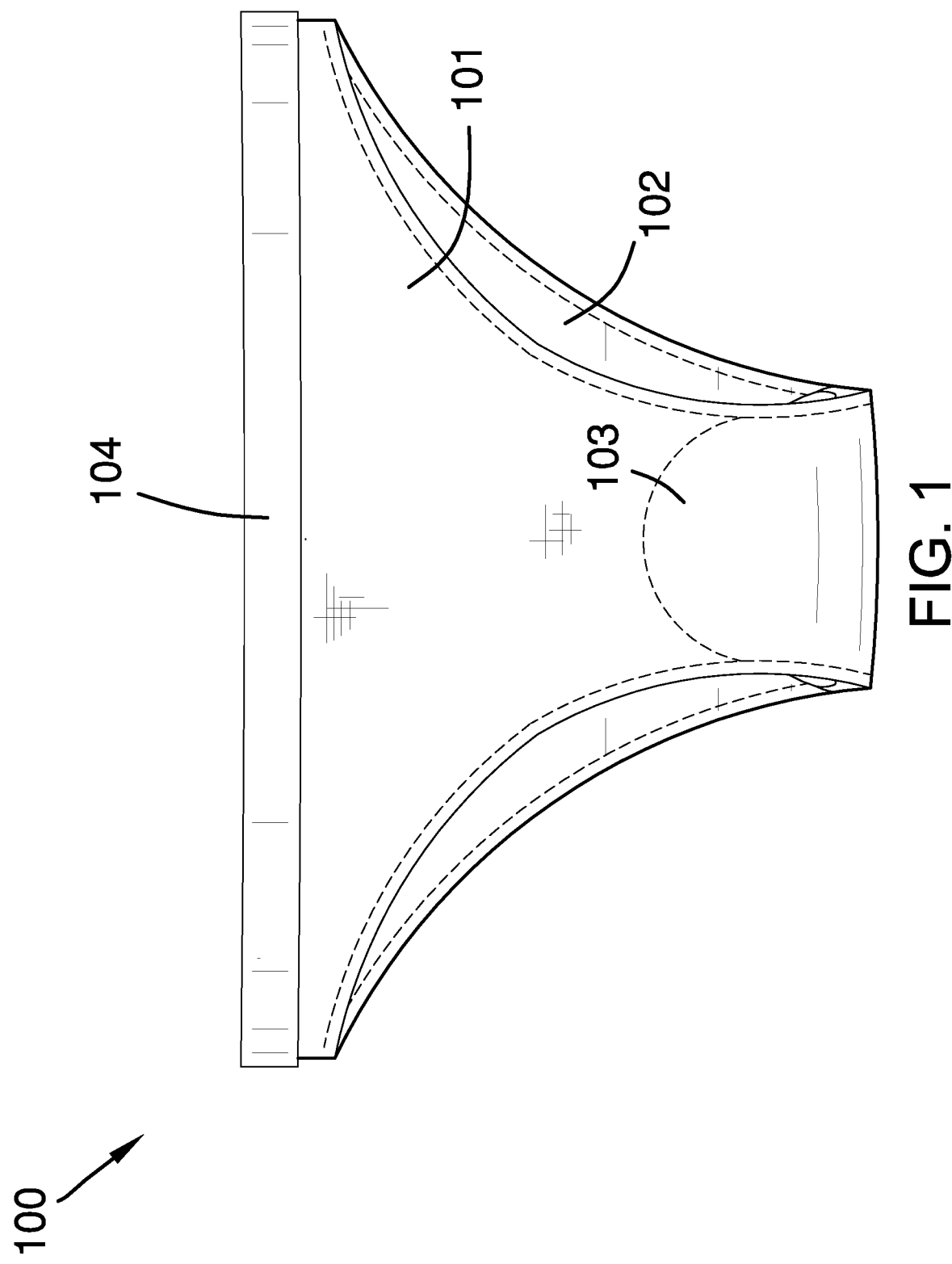
FIG. 1 is a front view of an embodiment of the disclosure.
Figure 2:
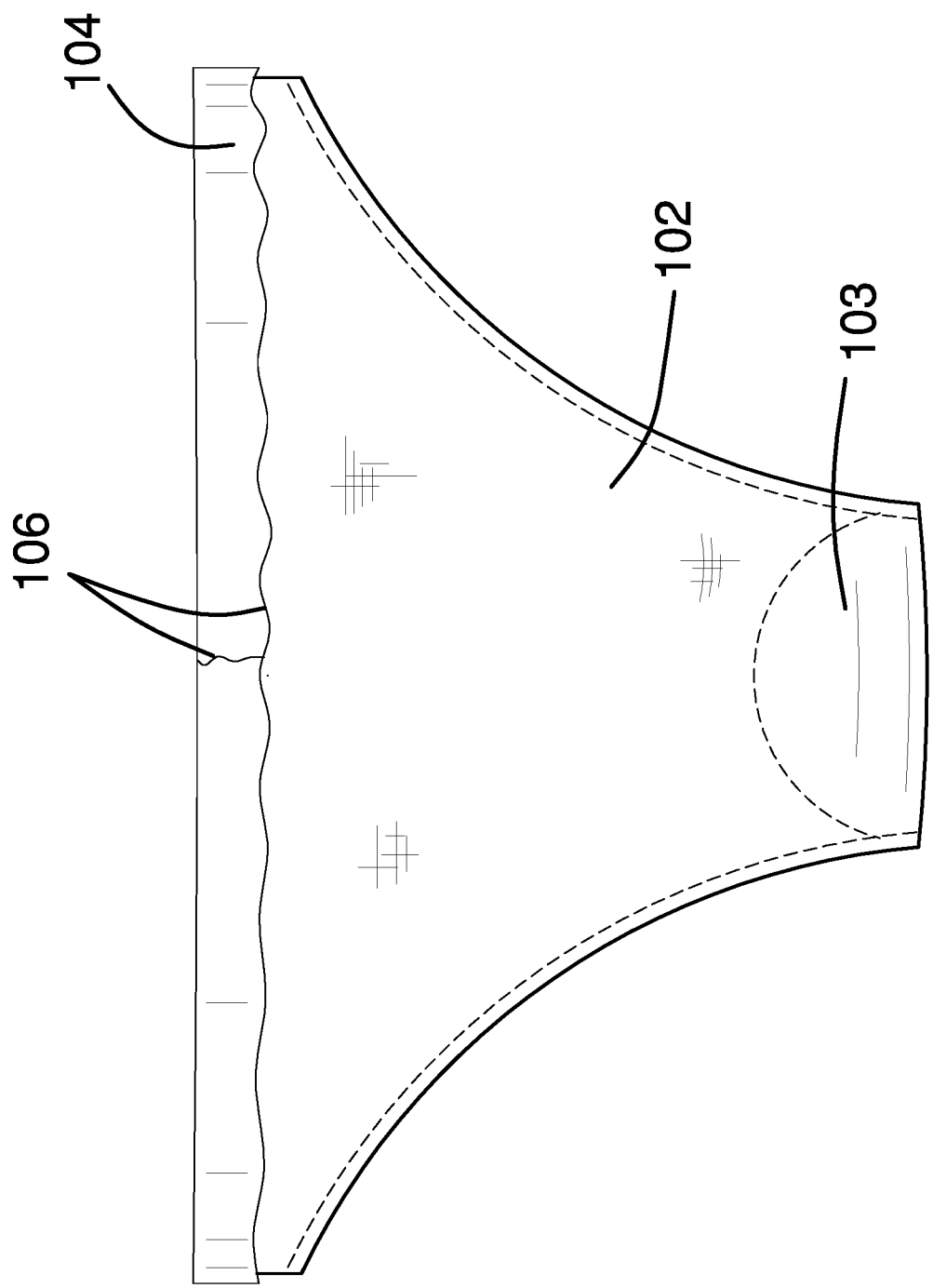
FIG. 2 is a rear view of an embodiment of the disclosure.
Figure 3:
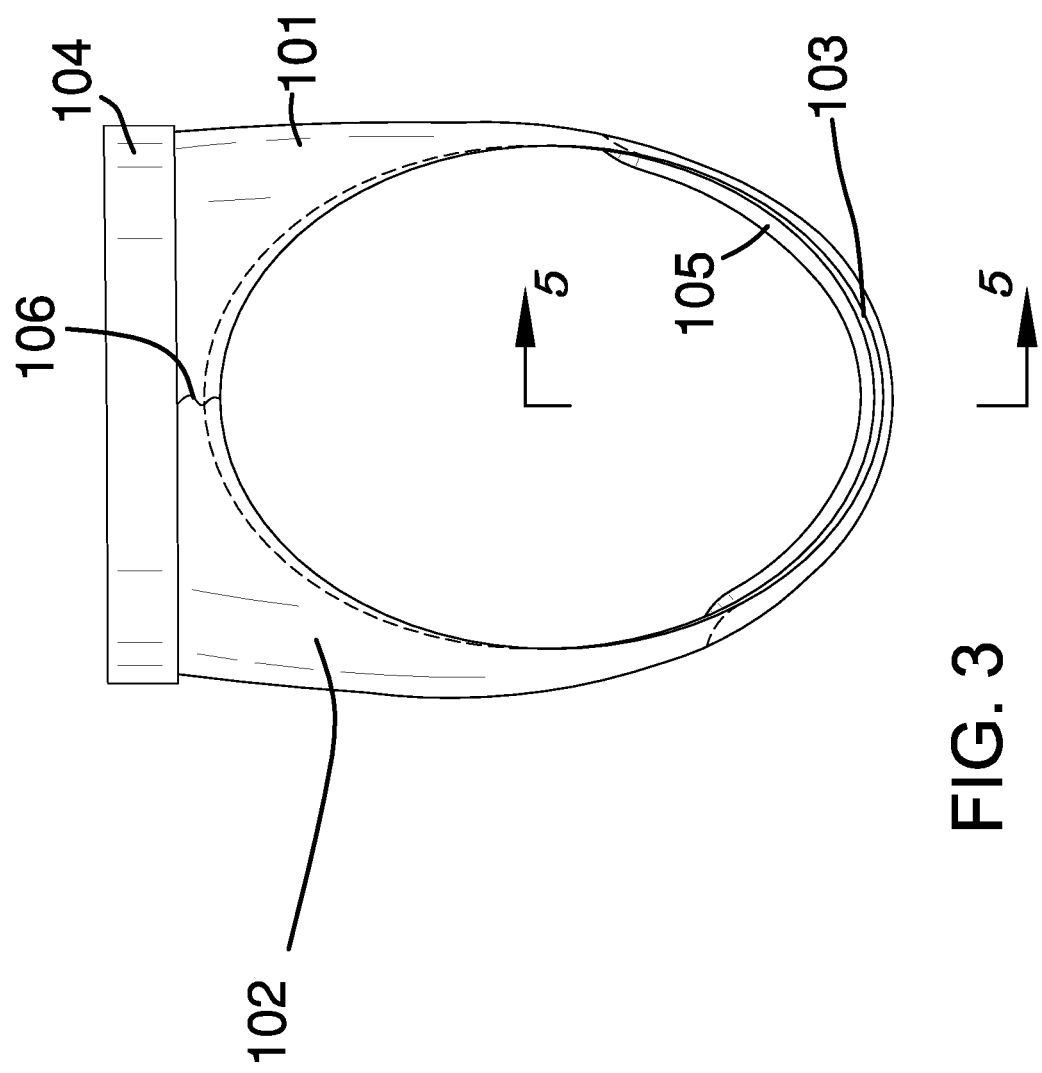
FIG. 3 is a side view of an embodiment of the disclosure.
Figure 4:
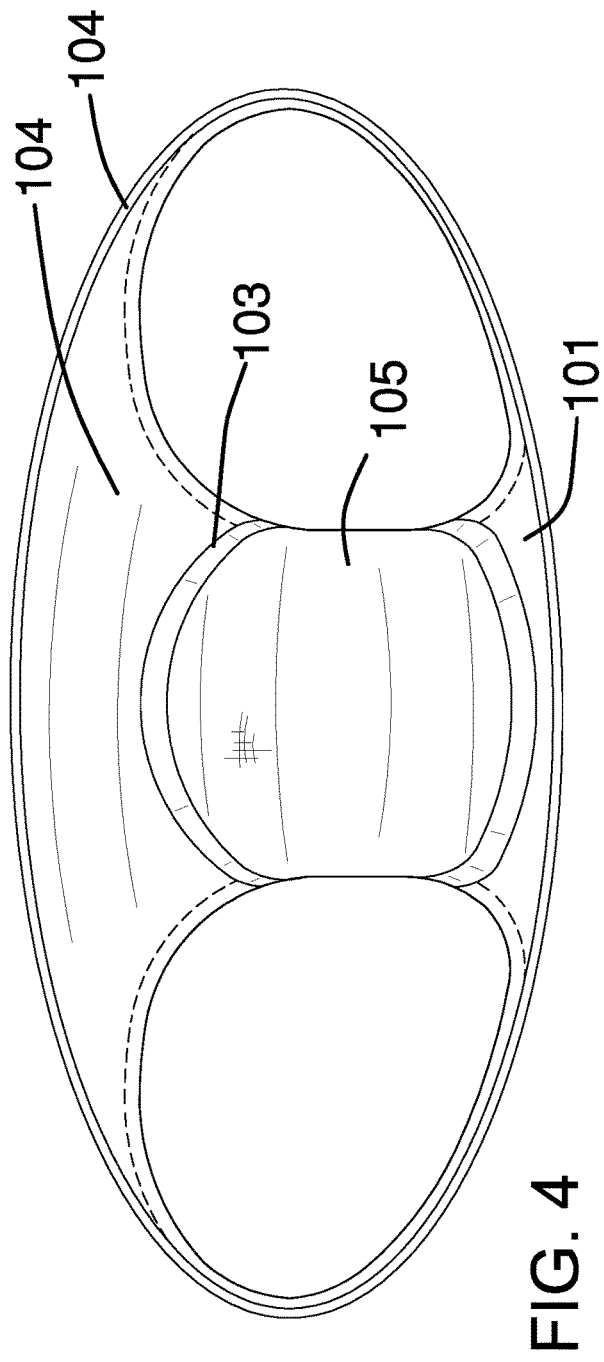
FIG. 4 is a top view of an embodiment of the disclosure.
Figure 5:
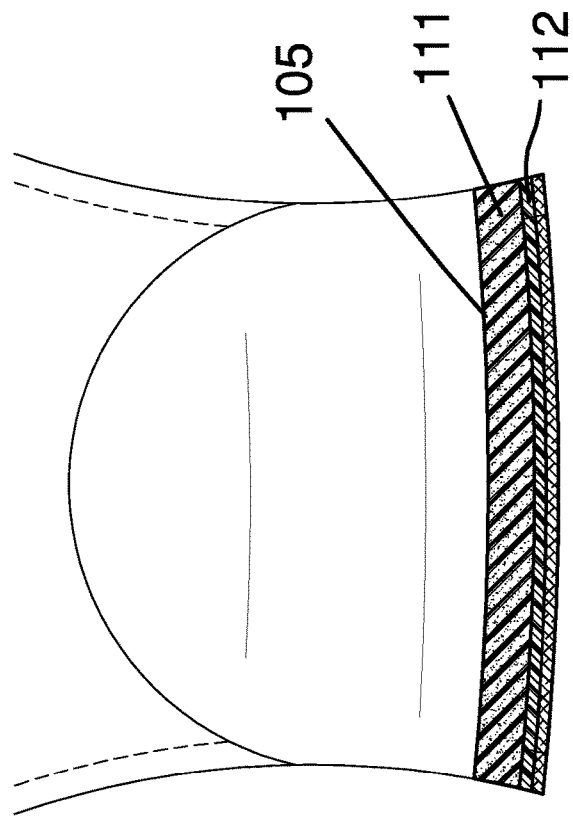
FIG. 5 is a cross-sectional view of an embodiment of the disclosure across 5-5 as shown in FIG. 3.
Figure 6:
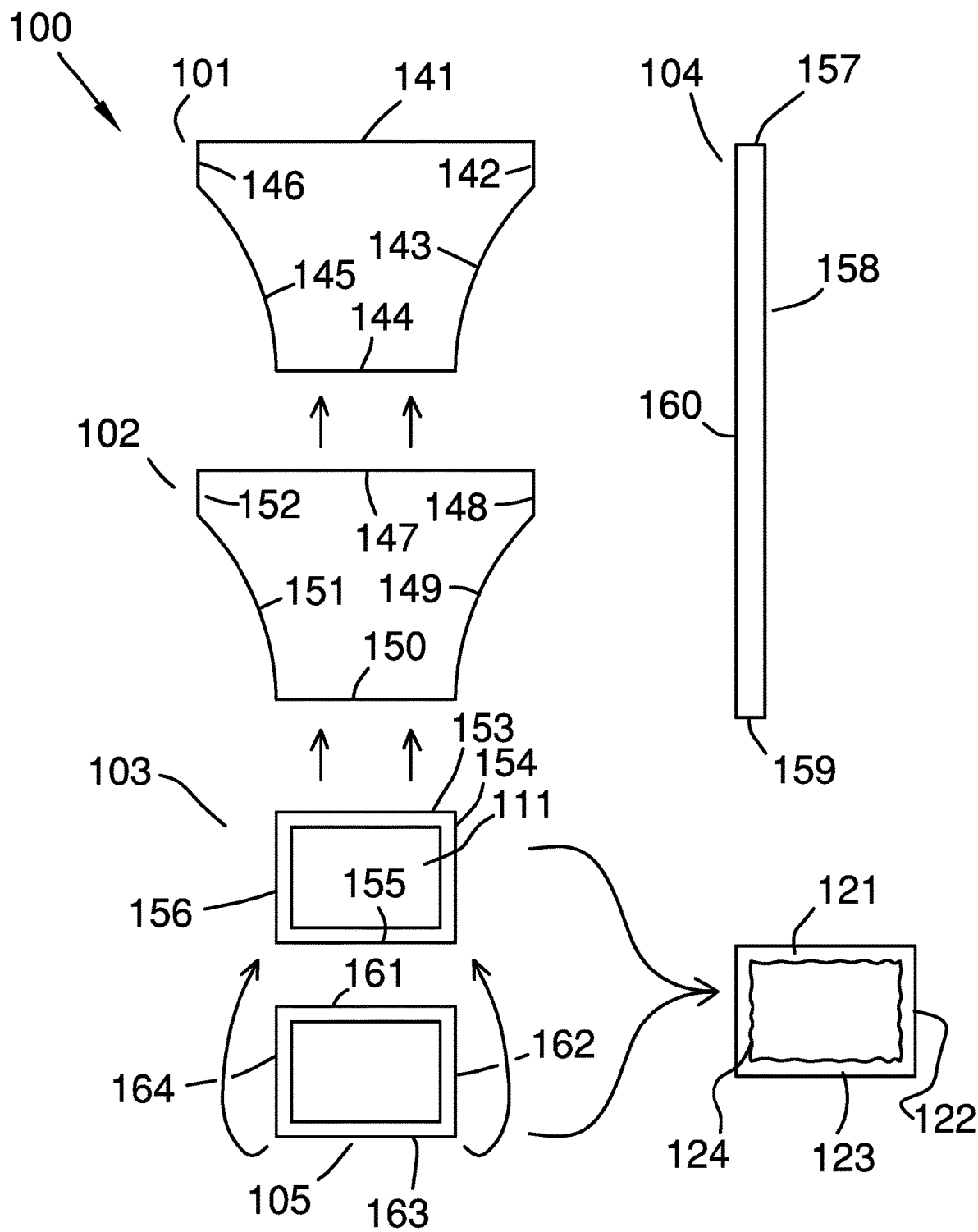
FIG. 6 is an exploded view of an embodiment of the disclosure.
Figure 7:
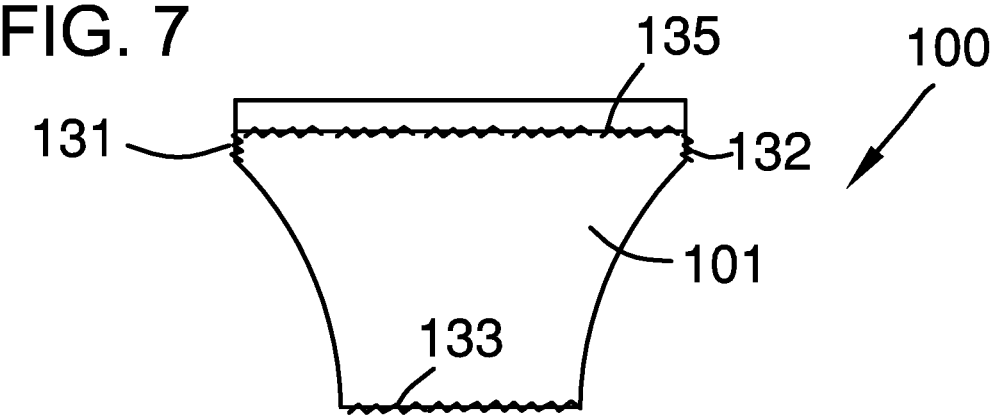
FIG. 7 is a front view of an embodiment of the disclosure.
Figure 8:
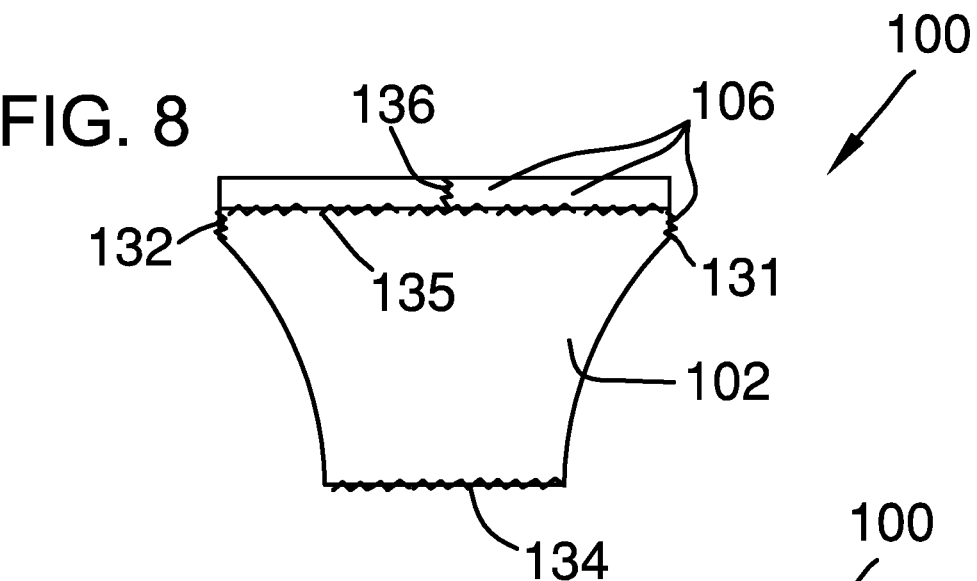
FIG. 8 is a rear view of an embodiment of the disclosure.
Figure 9:
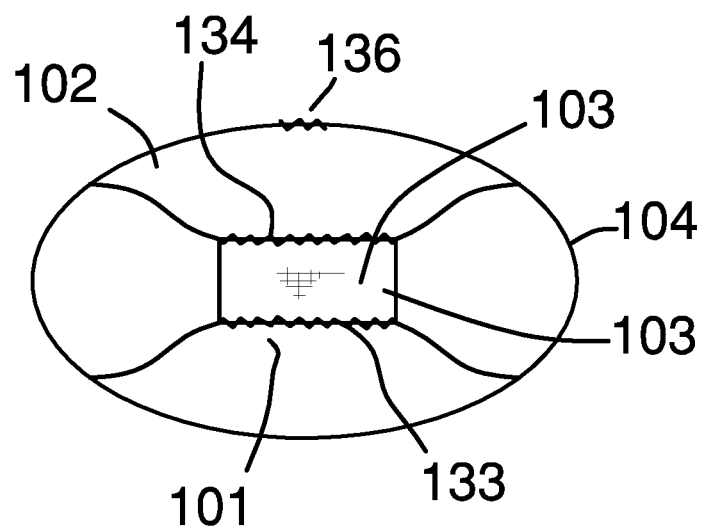
FIG. 9 is a top view of an embodiment of the disclosure.

Detailed reference will now be made to one or more potential embodiments of the disclosure, which are illustrated in FIGS. 1 through 9.

The undergarment with an integral sanitary liner 100 (hereinafter invention) is an article of loin wear. The invention 100 is adapted for use by a patient. The patient wears the invention 100 when the patient anticipates liquid discharge in the loin region. The invention 100 is an absorbent structure that absorbs liquid discharges in the loin region. The invention 100 is a reusable structure that is machine washable.

The invention 100 comprises an anterior panel 101, a posterior panel 102, an inferior panel 103, an elastic webbing 104, a liner 105, and a plurality of seams 106. The plurality of seams 106 interconnect the anterior panel 101, the posterior panel 102, the inferior panel 103, and the elastic webbing 104 to form the article of loin wear. The inferior panel 103 forms the absorbent structure of the invention 100. The liner 105 is a sheeting that protects the patient from the liquids accumulated by the inferior panel 103. The article of loin wear is machine washable.

The anterior panel 101 is a textile. The anterior panel 101 is cut with six sides. The anterior panel 101 covers the anterior, dexter and sinister loin regions of the patient. The anterior panel 101 comprises a first edge 141, a second edge 142, a third edge 143, a fourth edge 144, a fifth edge 145, and a sixth edge 146.

The first edge 141 is a straight edge of the anterior panel 101. The first edge 141 forms a vertex with the sixth edge 146 of the anterior panel 101. The first edge 141 forms a vertex with the second edge 142 of the anterior panel 101.

The second edge 142 is a straight edge of the anterior panel 101. The second edge 142 forms a vertex with the first edge 141 of the anterior panel 101. The second edge 142 forms a vertex with the third edge 143 of the anterior panel 101.

The third edge 143 is a curved edge of the anterior panel 101. The third edge 143 forms a vertex with the second edge 142 of the anterior panel 101. The third edge 143 forms a vertex with the fourth edge 144 of the anterior panel 101.

The fourth edge 144 is a straight edge of the anterior panel 101. The fourth edge 144 forms a vertex with the third edge 143 of the anterior panel 101. The fourth edge 144 forms a vertex with the fifth edge 145 of the anterior panel 101.

The fifth edge 145 is a curved edge of the anterior panel 101. The fifth edge 145 forms a vertex with the fourth edge 144 of the anterior panel 101. The fifth edge 145 forms a vertex with the sixth edge 146 of the anterior panel 101.

The sixth edge 146 is a straight edge of the anterior panel 101. The sixth edge 146 forms a vertex with the fifth edge 145 of the anterior panel 101. The sixth edge 146 forms a vertex with the first edge 141 of the anterior panel 101.

The posterior panel 102 is a textile. The posterior panel 102 is cut with six sides. The posterior panel 102 covers the posterior, dexter and sinister loin regions of the patient. The posterior panel 102 comprises a seventh edge 147, an eighth edge 148, a ninth edge 149, a tenth edge 150, an eleventh edge 151, and a twelfth edge 152.

The seventh edge 147 is a straight edge of the posterior panel 102. The seventh edge 147 forms a vertex with the twelfth edge 152 of the posterior panel 102. The seventh edge 147 forms a vertex with the eighth edge 148 of the posterior panel 102.

The eighth edge 148 is a straight edge of the posterior panel 102. The eighth edge 148 forms a vertex with the seventh edge 147 of the posterior panel 102. The eighth edge 148 forms a vertex with the ninth edge 149 of the posterior panel 102.

The ninth edge 149 is a curved edge of the posterior panel 102. The ninth edge 149 forms a vertex with the eighth edge 148 of the posterior panel 102. The ninth edge 149 forms a vertex with the tenth edge 150 of the posterior panel 102.

The tenth edge 150 is a straight edge of the posterior panel 102. The tenth edge 150 forms a vertex with the ninth edge 149 of the posterior panel 102. The tenth edge 150 forms a vertex with the eleventh edge 151 of the posterior panel 102.

The eleventh edge 151 is a curved edge of the posterior panel 102. The eleventh edge 151 forms a vertex with the tenth edge 150 of the posterior panel 102. The eleventh edge 151 forms a vertex with the twelfth edge 152 of the posterior panel 102.

The twelfth edge 152 is a straight edge of the posterior panel 102. The twelfth edge 152 forms a vertex with the eleventh edge 151 of the posterior panel 102. The twelfth edge 152 forms a vertex with the seventh edge 147 of the posterior panel 102.

The inferior panel 103 is a textile. The inferior panel 103 is cut with four sides. The inferior panel 103 covers the inferior loin region of the patient. The inferior panel 103 accumulates and stores any liquids discharged by the patient. The inferior panel 103 comprises a thirteenth edge 153, a fourteenth edge 154, a fifteenth edge 155, and a sixteenth edge 156.

The inferior panel 103 further comprises a plush structure 111 and a fluid impermeable liner 112. The plush structure 111 is a napped textile structure. The plush structure 111 forms the physical structure that stores the liquid discharged by the patient. The fluid impermeable liner 112 is a fluid impermeable sheeting. The fluid impermeable liner 112 permanently attaches the plush structure 111 to the interior surface of the inferior panel 103 such that the fluid impermeable liner 112 inhibits the flow of the liquid discharged by the patient from the plush structure 111 into the inferior panel 103.

The thirteenth edge 153 is a straight edge of the inferior panel 103. The thirteenth edge 153 forms a vertex with the sixteenth edge 156 of the inferior panel 103. The thirteenth edge 153 forms a vertex with the fourteenth edge 154 of the inferior panel 103.

The fourteenth edge 154 is a straight edge of the inferior panel 103. The fourteenth edge 154 forms a vertex with the thirteenth edge 153 of the inferior panel 103. The fourteenth edge 154 forms a vertex with the fifteenth edge 155 of the inferior panel 103.

The fifteenth edge 155 is a straight edge of the inferior panel 103. The fifteenth edge 155 forms a vertex with the fourteenth edge 154 of the inferior panel 103. The fifteenth edge 155 forms a vertex with the sixteenth edge 156 of the inferior panel 103.

The sixteenth edge 156 is a straight edge of the inferior panel 103. The sixteenth edge 156 forms a vertex with the fifteenth edge 155 of the inferior panel 103. The sixteenth edge 156 forms a vertex with the thirteenth edge 153 of the inferior panel 103.

The elastic webbing 104 is an elastic webbing 104. The elastic webbing is formed with four edges. The elastic webbing 104 forms a waistband that secures the invention 100 to the patient. The elastic webbing 104 acts as a spring. Specifically, when a force is applied to both ends of the elastic webbing 104 in a direction parallel to the major axis of the elastic webbing 104, the applied force elongates the span of the end to end length the elastic webbing 104 in the direction parallel to the major axis of the elastic webbing 104. The elasticity of the elastic webbing 104 creates a force that opposes the displacement created by the applied force. The elasticity of the elastic webbing 104 returns the elastic webbing 104 to return to its relaxed shape.

When the elongated elastic webbing 104 is wrapped around a patient, the patient will prevent the elastic webbing 104 from returning to its relaxed shape. In this circumstance, the elastic webbing 101 will apply a force projecting radially away from the center axis of the elastic webbing 104 and through the lateral face of the elastic webbing 101 and against the patient that binds the elastic webbing 104 to the patient.

The elastic webbing 104 comprises a seventeenth edge 157, an eighteenth edge 158, a nineteenth edge 159, and a twentieth edge 160.

The seventeenth edge 157 is a straight edge of the elastic webbing 104. The seventeenth edge 157 forms a vertex with the twentieth edge 160 of the elastic webbing 104. The seventeenth edge 157 forms a vertex with the eighteenth edge 158 of the elastic webbing 104.

The eighteenth edge 158 is a straight edge of the elastic webbing 104. The eighteenth edge 158 forms a vertex with the seventeenth edge 157 of the elastic webbing 104. The eighteenth edge 158 forms a vertex with the nineteenth edge 159 of the elastic webbing 104.

The nineteenth edge 159 is a straight edge of the elastic webbing 104. The nineteenth edge 159 forms a vertex with the eighteenth edge 158 of the elastic webbing 104. The nineteenth edge 159 forms a vertex with the twentieth edge 160 of the elastic webbing 104.

The twentieth edge 160 is a straight edge of the elastic webbing 104. The twentieth edge 160 forms a vertex with the nineteenth edge 159 of the elastic webbing 104. The twentieth edge 160 forms a vertex with the seventeenth edge 157 of the elastic webbing 104.

The liner 105 is a textile. The liner 105 is cut with four sides. The liner 105 encloses the plush structure 111 of the inferior panel 103 that is proximal to the patient. The liner 105 forms a wicking structure that uses capillary action to wick the discharged liquids away from the patient into the inferior panel 103. Methods to form a wicking textile are well-known and documented in the textile arts. The liner 105 comprises a twenty-first edge 161, a twenty-second edge 162, a twenty-third edge 163, and a twenty-fourth edge 164.

The twenty-first edge 161 is a straight edge of the liner 105. The twenty-first edge 161 forms a vertex with the twenty-fourth edge 164 of the liner 105. The twenty-first edge 161 forms a vertex with the twenty-second edge 162 of the liner 105.

The twenty-second edge 162 is a straight edge of the liner 105. The twenty-second edge 162 forms a vertex with the twenty-first edge 161 of the liner 105. The twenty-second edge 162 forms a vertex with the twenty-third edge 163 of the liner 105.

The twenty-third edge 163 is a straight edge of the liner 105. The twenty-third edge 163 forms a vertex with the twenty-second edge 162 of the liner 105. The twenty-third edge 163 forms a vertex with the twenty-fourth edge 164 of the liner 105.

The twenty-fourth edge 164 is a straight edge of the liner 105. The twenty-fourth edge 164 forms a vertex with the twenty-third edge 163 of the liner 105. The twenty-fourth edge 164 forms a vertex with the twenty-first edge 161 of the liner 105.

The liner 105 further comprises a seventh seam 121, a eighth seam 122, a ninth seam 123, and a tenth seam 124.

The seventh seam 121 is a sewn seam that attaches the liner 105 to the inferior panel 103 such that the liner 105 encloses the plush structure 111. The seventh seam 121 is applied parallel to the twenty-first edge 161 of the liner 105. The seventh seam 121 is the sewn seam that is proximal to the twenty-first edge 161 of the liner 105.

The eighth seam 122 is a sewn seam that attaches the liner 105 to the inferior panel 103 such that the liner 105 encloses the plush structure 111. The eighth seam 122 is applied parallel to the twenty-second edge 162 of the liner 105. The eighth seam 122 is the sewn seam that is proximal to the twenty-second edge 162 of the liner 105.

The ninth seam 123 is a sewn seam that attaches the liner 105 to the inferior panel 103 such that the liner 105 encloses the plush structure 111. The ninth seam 123 is applied parallel to the twenty-third edge 163 of the liner 105. The ninth seam 123 is the sewn seam that is proximal to the twenty-third edge 163 of the liner 105.

The tenth seam 124 is a sewn seam that attaches the liner 105 to the inferior panel 103 such that the liner 105 encloses the plush structure 111. The tenth seam 124 is applied parallel to the twenty-fourth edge 164 of the liner 105. The tenth seam 124 is the sewn seam that is proximal to the twenty-fourth edge 164 of the liner 105.

Each of the plurality of seams 106 is a seam. Each of the plurality of seams 106 attaches an initial edge of a first textile structure selected from the group consisting of the anterior panel 101, the posterior panel 102, the inferior panel 103, and the elastic webbing 104 to a subsequent edge of a second textile structure selected from the group consisting of the anterior panel 101, the posterior panel 102, the inferior panel 103, and the elastic webbing 104. The plurality of seams 106 further comprises a first seam 131, a second seam 132, a third seam 133, a fourth seam 134, a fifth seam 135, and a sixth seam 136. In the first potential embodiment of the disclosure, the first seam 131 is a sewn seam. The second seam 132 is a sewn seam. The third seam 133 is a sewn seam. The fourth seam 134 is a sewn seam. The fifth seam 135 is a sewn seam. The sixth seam 136 is a sewn seam.

The following four paragraphs describe the assembly of the invention 100.

The first seam 131 attaches the sixth edge 146 of the anterior panel 101 to the twelfth edge 152 of the posterior panel 102. The second seam 132 attaches the second edge 142 of the anterior panel 101 to the eighth edge 148 of the posterior panel 102. The third seam 133 attaches the fourth edge 144 of the anterior panel 101 to the fifteenth edge 155 of the inferior panel 103. The fourth seam 134 attaches the tenth edge 150 of the posterior panel 102 to the thirteenth edge 153 of the inferior panel 103.

The fifth seam 135 attaches the eighteenth edge 158 of the elastic webbing 104 to the first edge 141 of the anterior panel 101 and the seventh edge 147 of the posterior panel 102. The fifth seam 135 attaches the elastic webbing 104 to the anterior panel 101 and the posterior panel 102 while the elastic webbing 104 is held under tension in the direction of the major axis.

The sixth seam 136 attaches the seventeenth edge 157 of the elastic webbing 104 to the nineteenth edge 159 of the elastic webbing 104.

The liner 105 encloses the plush structure 111 of the liner 105 by: a) using the seventh seam 121 to attach the twenty-first edge 161 of the liner 105 to the thirteenth edge 153 of the inferior panel 103; b) using the tenth seam 124 to attach the twenty-fourth edge 164 of the liner 105 to the fourteenth edge 154 of the inferior panel 103; c) using the ninth seam 123 to attach the twenty-third edge 163 of the liner 105 to the fifteenth edge 155 of the inferior panel 103; and, d) using the eighth seam 122 to attach the twenty-second edge 162 of the elastic webbing 104 to the sixteenth edge 156 of the inferior panel 103.

To wash the invention 100, the liner 105 is removed from the inferior panel 103. The invention 100 is then launderable.

The following definitions were used in this disclosure:

Absorbent: As used in this disclosure, absorbent is an adjective that refers to a material that is able to soak up a liquid such as water.

Anterior: As used in this disclosure, anterior is a term that is used to refer to the front side or direction of a structure. When comparing two objects, the anterior object is the object that is closer to the front of the structure.

Bind: As used in this disclosure, to bind is a verb that means to tie or secure a first object to a second object using a strap, cord or webbing.

Capillary Action: As used in this disclosure, capillary action refers to the tendency of a liquid to experience adhesion forces when exposed to surface or surfaces formed within a narrow structure and the tendency of a liquid to flow as a result of these adhesion force. In the proper circumstances, the adhesive forces of capillary action can overcome gravitational forces or the intermolecular forces that form liquids. The span of the lengths where capillary action predominates is often referred to as a microfluidic scale. On a practical level, the concept of wicking and wicking fabrics rely primarily on capillary action.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Dexter: As used in this disclosure, dexter is a directional reference that refers to the right side of the body or the right side of an object from the perspective of a viewer who is facing the posterior side of the object.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Textile: As used in this disclosure, an elastic textile is a textile that contains elastic yarns as some of the yarns that make up the textile. An elastic textile is constructed such that the elastic textile will stretch when a force is applied and will return to its original shape when after the force is removed.

Elastic Webbing: As used in this disclosure, an elastic webbing is a webbing that contains elastic yarns as some of the yarns that make up the webbing. An elastic webbing is constructed such that the elastic webbing will stretch when a force is applied and will return to its original shape when after the force is removed.

Fluid: As used in this disclosure, a fluid refers to a state of matter wherein the matter is capable of flow and takes the shape of a container it is placed within. The term fluid commonly refers to a liquid or a gas.

Inferior: As used in this disclosure, inferior refers to a directional sense or location of the body. Specifically, inferior refers to an object or a side of an object that is proximal to the feet or distal from the head of the body.

Lateral: As used in this disclosure, lateral refers to a directional sense or location of the body. Specifically, lateral refers to an object or a side of an object that is proximal to the side that is distal from the medial axis of the body.

Liner: As used in this disclosure, a liner is a structure that is positioned between a first object and a second object such that the first object and the second object will not damage each other.

Liquid: As used in this disclosure, a liquid refers to a state (phase) of matter that is fluid and that maintains, for a given pressure, a fixed volume that is independent of the volume of the container.

Loin: As used in this disclosure, the loin refers to a region of the human body that comprises the pelvis, the buttocks, and the adjacent reproductive organs.

Loin Wear: As used in this disclosure, loin wear refers to underclothing that is intended to be worn over the loin region with the occasional exception of the buttocks. Commonly used synonyms for loin wear include, but are not limited to, bikini bottoms, boxer briefs, boxers, briefs, calzones, drawers, French cut, g string, knickers, loincloth, panties, panty, shorts, skivvies, thong, trunks, underpants, undies, and unmentionables.

Major and Minor Axes: As used in this disclosure, the major and minor axes refer to a pair of perpendicular axes that are defined within a structure. The length of the major axis is always greater than or equal to the length of the minor axis. The major axis is always the longest diameter of the structure. The major and minor axes intersect at the center of the structure. The major axis is always parallel to an edge of a rectangular or rectilinear structure.

Medial: As used in this disclosure, medial refers to a directional sense or location of the body. Specifically, medial refers to a first object or a side of a first object that is closer to the medial axis or more distal from the side of the body relative to a second object or side of a second object.

Nap: As used in this disclosure, a nap refers to one or more loose yarns that are incorporated in a textile such that the separated, or "raised," from the plane of the primary surface of a textile. A nap may: 1) take the form of a loop; or 2) take the form of loose "ends" extending beyond the textile. Within this disclosure, the terms pile and nap may considered synonyms. A textile comprising a plurality of napped yarns is often referred to as a plush textile.

Pad: As used in this disclosure, a pad is a mass of soft material used as a filling or for protection against damage or injury.

Patient: As used in this disclosure, a patient is a person who is designated to receive a medical treatment, therapy or service. The term patient may be extended to an animal when used within the context of the animal receiving veterinary treatment or services.

Pelvis: As used in this disclosure, the pelvis refers to a bone structure near the base of the spine to which buttocks and the legs are joined. As used in this disclosure, the term pelvis is a more generally expanded to describe the above described region of the body. As used in this disclosure, the adjectival form of pelvis is pelvic.

Posterior: As used in this disclosure, posterior is a term that is used to refer to the side of an object that is distal or in the opposite direction of the anterior side. When comparing two items, the posterior item is the item that is distal from the anterior of the object.

Relaxed Shape: As used in this disclosure, a structure is considered to be in its relaxed state when no shear, strain, or torsional forces are being applied to the structure.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Sheeting: As used in this disclosure, a sheeting is a material, such as a paper, textile, a plastic, or a metal foil, in the form of a thin flexible layer or layers.

Sinister: As used in this disclosure, sinister is a directional reference that refers to the left side of the body or the left side of an object from the perspective of a viewer who is facing the posterior side of the object.

Superior: As used in this disclosure, superior refers to a directional sense or location of the body. Specifically, superior refers to an object or a side of an object that is distal from the feet or proximal to the head of the body.

Textile: As used in this disclosure, a textile is a material that is woven, knitted, braided or felted. Synonyms in common usage for this definition include fabric and cloth.

Vertex: As used in this disclosure, a vertex (plural vertices) is an angle that is formed by two lines that form a point. Vertices are commonly found in polygons.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips. Webbings have tensile strength but are too flexible to provide compressive strength and are not suitable for use in pushing objects. The two surfaces of a webbing with the greatest surface area are called the faces of the webbing.

Wick: As used in this disclosure, a wick is textile material that uses capillary action to draw a liquid out of a reservoir for subsequent use. The use of wicks is well-known and documented in the chemical arts. The process of drawing a liquid through a wick is commonly called wicking.

With respect to the above description, it is to be realized that the optimum dimensional relationship for the various components of the invention described above and in FIGS. 1 through 9 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A garment comprising:
an anterior panel, a posterior panel, an inferior panel, an elastic webbing, a liner, and a plurality of seams;
wherein the plurality of seams interconnect the anterior panel, the posterior panel, the inferior panel, and the elastic webbing to form an article of loin wear;
wherein the garment is an absorbent structure that absorbs liquid discharges;
wherein the garment is a reusable structure;
wherein the garment is machine washable;
wherein the inferior panel forms the absorbent structure of the garment;
wherein the plurality of seams further comprises a first seam, a second seam, a third seam, a fourth seam, a fifth seam, and a sixth seam;
wherein the liner is a sheeting;
wherein the anterior panel is a textile;
wherein the posterior panel is a textile;
wherein the inferior panel is a textile;
wherein the liner is a textile;
wherein the anterior panel is cut with six sides;
wherein the posterior panel is cut with six sides;
wherein the inferior panel is cut with four sides;
wherein the elastic webbing is formed with four edges; and
wherein the liner is cut with four sides.

2. The garment according to claim 1
wherein the inferior panel further comprises a plush structure and a fluid impermeable liner; and
wherein the fluid impermeable liner is a fluid impermeable sheeting.

3. The garment according to claim 2
wherein the plush structure is a napped textile structure;
wherein the plush structure forms the physical structure that stores the discharged liquid; and
wherein the fluid impermeable liner permanently attaches the plush structure to an interior surface of the inferior panel such that the fluid impermeable liner inhibits a flow of the discharged liquid into the inferior panel.

4. The garment according to claim 3
wherein the elastic webbing forms a waistband; and
wherein a force applied to both ends of the elastic webbing in a direction parallel to a major axis of the elastic webbing elongates the span of the end to end length of the elastic webbing in a direction parallel to the major axis of the elastic webbing.

5. The garment according to claim 4
wherein the liner encloses the plush structure of the inferior panel; and
wherein the liner forms a wicking structure that uses capillary action to wick the discharged liquids into the inferior panel.

6. The garment according to claim 5
wherein the liner further comprises a seventh seam, a eighth seam, a ninth seam, and a tenth seam;
wherein the seventh seam is a sewn seam that attaches the liner to the inferior panel such that the liner encloses the plush structure;
wherein the eighth seam is a sewn seam that attaches the liner to the inferior panel such that the liner encloses the plush structure;
wherein the ninth seam is a sewn seam that attaches the liner to the inferior panel such that the liner encloses the plush structure; and
wherein the tenth seam is a sewn seam that attaches the liner to the inferior panel such that the liner encloses the plush structure.

7. The garment according to claim 6
wherein the anterior panel comprises a first edge, a second edge, a third edge, a fourth edge, a fifth edge, and a sixth edge;
wherein the first edge is a straight edge of the anterior panel;
wherein the first edge forms a vertex with the sixth edge of the anterior panel;
wherein the first edge forms a vertex with the second edge of the anterior panel;

wherein the second edge is a straight edge of the anterior panel;

wherein the second edge forms a vertex with the first edge of the anterior panel;

wherein the second edge forms a vertex with the third edge of the anterior panel;

wherein the third edge is a curved edge of the anterior panel;

wherein the third edge forms a vertex with the second edge of the anterior panel;

wherein the third edge forms a vertex with the fourth edge of the anterior panel;

wherein the fourth edge is a straight edge of the anterior panel;

wherein the fourth edge forms a vertex with the third edge of the anterior panel;

wherein the fourth edge forms a vertex with the fifth edge of the anterior panel;

wherein the fifth edge is a curved edge of the anterior panel;

wherein the fifth edge forms a vertex with the fourth edge of the anterior panel;

wherein the fifth edge forms a vertex with the sixth edge of the anterior panel;

wherein the sixth edge is a straight edge of the anterior panel;

wherein the sixth edge forms a vertex with the fifth edge of the anterior panel; and wherein the sixth edge forms a vertex with the first edge of the anterior panel.

8. The garment according to claim 7 wherein the posterior panel comprises a seventh edge, an eighth edge, a ninth edge, a tenth edge, an eleventh edge, and a twelfth edge;

wherein the seventh edge is a straight edge of the posterior panel;

wherein the seventh edge forms a vertex with the twelfth edge of the posterior panel;

wherein the seventh edge forms a vertex with the eighth edge of the posterior panel;

wherein the eighth edge is a straight edge of the posterior panel;

wherein the eighth edge forms a vertex with the seventh edge of the posterior panel;

wherein the eighth edge forms a vertex with the ninth edge of the posterior panel;

wherein the ninth edge is a curved edge of the posterior panel;

wherein the ninth edge forms a vertex with the eighth edge of the posterior panel;

wherein the ninth edge forms a vertex with the tenth edge of the posterior panel;

wherein the tenth edge is a straight edge of the posterior panel;

wherein the tenth edge forms a vertex with the ninth edge of the posterior panel;

wherein the tenth edge forms a vertex with the eleventh edge of the posterior panel;

wherein the eleventh edge is a curved edge of the posterior panel;

wherein the eleventh edge forms a vertex with the tenth edge of the posterior panel;

wherein the eleventh edge forms a vertex with the twelfth edge of the posterior panel;

wherein the twelfth edge is a straight edge of the posterior panel;

wherein the twelfth edge forms a vertex with the eleventh edge of the posterior panel; and wherein the twelfth edge forms a vertex with the seventh edge of the posterior panel.

9. The garment according to claim 8 wherein the inferior panel comprises a thirteenth edge, a fourteenth edge, a fifteenth edge, and a sixteenth edge;

wherein the thirteenth edge is a straight edge of the inferior panel;

wherein the thirteenth edge forms a vertex with the sixteenth edge of the inferior panel;

wherein the thirteenth edge forms a vertex with the fourteenth edge of the inferior panel;

wherein the fourteenth edge is a straight edge of the inferior panel;

wherein the fourteenth edge forms a vertex with the thirteenth edge of the inferior panel;

wherein the fourteenth edge forms a vertex with the fifteenth edge of the inferior panel;

wherein the fifteenth edge is a straight edge of the inferior panel;

wherein the fifteenth edge forms a vertex with the fourteenth edge of the inferior panel;

wherein the fifteenth edge forms a vertex with the sixteenth edge of the inferior panel;

wherein the sixteenth edge is a straight edge of the inferior panel;

wherein the sixteenth edge forms a vertex with the fifteenth edge of the inferior panel; and wherein the sixteenth edge forms a vertex with the thirteenth edge of the inferior panel.

10. The garment according to claim 9 wherein the elastic webbing comprises a seventeenth edge, an eighteenth edge, a nineteenth edge, and a twentieth edge;

wherein the seventeenth edge is a straight edge of the elastic webbing;

wherein the seventeenth edge forms a vertex with the twentieth edge of the elastic webbing;

wherein the seventeenth edge forms a vertex with the eighteenth edge of the elastic webbing;

wherein the eighteenth edge is a straight edge of the elastic webbing;

wherein the eighteenth edge forms a vertex with the seventeenth edge of the elastic webbing;

wherein the eighteenth edge forms a vertex with the nineteenth edge of the elastic webbing;

wherein the nineteenth edge is a straight edge of the elastic webbing;

wherein the nineteenth edge forms a vertex with the eighteenth edge of the elastic webbing;

wherein the nineteenth edge forms a vertex with the twentieth edge of the elastic webbing;

wherein the twentieth edge is a straight edge of the elastic webbing;

wherein the twentieth edge forms a vertex with the nineteenth edge of the elastic webbing; and wherein the twentieth edge forms a vertex with the seventeenth edge of the elastic webbing.

11. The garment according to claim 10 wherein the liner comprises a twenty-first edge, a twenty-second edge, a twenty-third edge, and a twenty-fourth edge;

wherein the twenty-first edge is a straight edge of the liner;

wherein the twenty-first edge forms a vertex with the twenty-fourth edge of the liner;

wherein the twenty-first edge forms a vertex with the twenty-second edge of the liner;
wherein the twenty-second edge is a straight edge of the liner;
wherein the twenty-second edge forms a vertex with the twenty-first edge of the liner;
wherein the twenty-second edge forms a vertex with the twenty-third edge of the liner;
wherein the twenty-third edge is a straight edge of the liner;
wherein the twenty-third edge forms a vertex with the twenty-second edge of the liner;
wherein the twenty-third edge forms a vertex with the twenty-fourth edge of the liner;
wherein the twenty-fourth edge is a straight edge of the liner;
wherein the twenty-fourth edge forms a vertex with the twenty-third edge of the liner; and
wherein the twenty-fourth edge forms a vertex with the twenty-first edge of the liner.

12. The garment according to claim 11
wherein the seventh seam is applied parallel to the twenty-first edge of the liner;
wherein the seventh seam is the sewn seam that is proximal to the twenty-first edge of the liner;
wherein the eighth seam is applied parallel to the twenty-second edge of the liner;
wherein the eighth seam is the sewn seam that is proximal to the twenty-second edge of the liner;
wherein the ninth seam is applied parallel to the twenty-third edge of the liner;
wherein the ninth seam is the sewn seam that is proximal to the twenty-third edge of the liner;
wherein the tenth seam is applied parallel to the twenty-fourth edge of the liner; and
wherein the tenth seam is the sewn seam that is proximal to the twenty-fourth edge of the liner.

13. The garment according to claim 12
wherein the first seam is a sewn seam;
wherein the second seam is a sewn seam;
wherein the third seam is a sewn seam;
wherein the fourth seam is a sewn seam;
wherein the fifth seam is a sewn seam; and
wherein the sixth seam is a sewn seam.

14. The garment according to claim 13
wherein the first seam attaches the sixth edge of the anterior panel to the twelfth edge of the posterior panel;
wherein the second seam attaches the second edge of the anterior panel to the eighth edge of the posterior panel;
wherein the third seam attaches the fourth edge of the anterior panel to the fifteenth edge of the inferior panel;
wherein the fourth seam attaches the tenth edge of the posterior panel to the thirteenth edge of the inferior panel;
wherein the fifth seam attaches the eighteenth edge of the elastic webbing to the first edge of the anterior panel and the seventh edge of the posterior panel;
wherein the fifth seam attaches the elastic webbing to the anterior panel and the posterior panel while the elastic webbing is held under tension in the direction of the major axis; and
wherein the sixth seam attaches the seventeenth edge of the elastic webbing to the nineteenth edge of the elastic webbing.

15. The garment according to claim 14
wherein the liner encloses the plush structure of the liner by using the seventh seam to attach the twenty-first edge of the liner to the thirteenth edge of the inferior panel;
wherein the liner encloses the plush structure of the liner by using the tenth seam to attach the twenty-fourth edge of the liner to the fourteenth edge of the inferior panel;
wherein the liner encloses the plush structure of the liner by using the ninth seam to attach the twenty-third edge of the liner to the fifteenth edge of the inferior panel; and
wherein the liner encloses the plush structure of the liner by using the eighth seam to attach the twenty-second edge of the elastic webbing to the sixteenth edge of the inferior panel.

16. The garment according to claim 15 wherein the garment is launderable.

* * * * *